United States Patent
Carter et al.

(10) Patent No.: US 8,110,001 B2
(45) Date of Patent: Feb. 7, 2012

(54) MATERIALS AND METHODS FOR IMPROVED BONE TENDON BONE TRANSPLANTATION

(75) Inventors: Kevin C. Carter, Gainesville, FL (US); Diane Carter, legal representative, Alachua, FL (US); Richard Ferguson, High Springs, FL (US)

(73) Assignee: RTI Biologics, Inc., Alachua, FL (US)

( * ) Notice: Subject to any disclaimer, the term of this patent is extended or adjusted under 35 U.S.C. 154(b) by 0 days.

(21) Appl. No.: 12/563,830

(22) Filed: Sep. 21, 2009

(65) Prior Publication Data
US 2010/0082104 A1    Apr. 1, 2010

Related U.S. Application Data

(63) Continuation of application No. 10/013,328, filed on Nov. 5, 2001, now abandoned, which is a continuation of application No. 09/924,110, filed on Aug. 7, 2001, now abandoned, which is a continuation-in-part of application No. 09/528,034, filed on Mar. 17, 2000, now Pat. No. 6,805,713, which is a continuation-in-part of application No. 09/481,319, filed on Jan. 11, 2000, now Pat. No. 6,497,726.

(51) Int. Cl.
*A61F 2/08* (2006.01)
(52) U.S. Cl. .................................................. 623/13.14
(58) Field of Classification Search ...... 623/13.11–13.2, 623/16.11, 17.11–17.16; 606/60
See application file for complete search history.

(56) References Cited

U.S. PATENT DOCUMENTS

| | | | |
|---|---|---|---|
| 4,870,957 A * | 10/1989 | Goble et al. | 623/13.12 |
| 5,067,962 A | 11/1991 | Campbell et al. | |
| 5,108,431 A * | 4/1992 | Mansat et al. | 623/13.14 |
| 5,151,104 A * | 9/1992 | Kenna | 606/328 |
| 5,152,790 A * | 10/1992 | Rosenberg et al. | 623/13.14 |
| 5,571,184 A * | 11/1996 | DeSatnick | 623/13.14 |
| 5,984,966 A * | 11/1999 | Kiema et al. | 623/13.14 |
| 5,989,253 A * | 11/1999 | Bigliardi | 623/13.14 |
| 6,190,411 B1 * | 2/2001 | Lo | 623/13.13 |
| 6,221,107 B1 * | 4/2001 | Steiner et al. | 623/13.14 |

(Continued)

FOREIGN PATENT DOCUMENTS

JP    10155820    8/1998

(Continued)

OTHER PUBLICATIONS

Japanese Patent Office, Notice of Reason for Rejection, in Japanese patent application No. 2006-279110, dated Apr. 4, 2011.

*Primary Examiner* — Alvin J Stewart
(74) *Attorney, Agent, or Firm* — McAndrews, Held & Malloy, Ltd.

(57) ABSTRACT

Disclosed herein is an improved Bone Tendon Bone graft for use in orthopedic surgical procedures. Specifically exemplified herein is a Bone Tendon Bone graft comprising one or more bone blocks having a groove cut into the surface thereof, wherein said groove is sufficient to accommodate a fixation screw. Also disclosed is a porcine bone tendon bone graft for use in orthopedic procedures. Also disclosed are multiple embodiments of assembled bone tendon bone blocks for use in orthopedic surgeries. Additionally, a method of harvesting grafts that has improved efficiency, increases the quantity of extracted tissue and minimizes time required by surgeon for implantation is disclosed.

10 Claims, 11 Drawing Sheets

U.S. PATENT DOCUMENTS

| | | | |
|---|---|---|---|
| 6,355,066 B1 * | 3/2002 | Kim | 623/13.14 |
| 6,579,295 B1 * | 6/2003 | Supinski | 623/13.14 |
| 6,780,187 B2 * | 8/2004 | Supinski | 623/13.14 |
| 7,008,451 B2 * | 3/2006 | Justin et al. | 623/13.14 |
| 7,083,647 B1 * | 8/2006 | Sklar et al. | 623/13.14 |
| 7,135,025 B2 * | 11/2006 | Pohjonen et al. | 606/321 |
| 7,137,996 B2 * | 11/2006 | Steiner et al. | 623/13.14 |
| 7,144,425 B2 * | 12/2006 | Steiner et al. | 623/13.14 |
| 7,172,595 B1 * | 2/2007 | Goble | 606/86 A |
| 7,235,100 B2 * | 6/2007 | Martinek | 623/13.14 |
| 7,588,586 B2 * | 9/2009 | Whittaker | 606/232 |
| 7,594,929 B2 * | 9/2009 | Collette | 623/13.14 |
| 7,648,524 B2 * | 1/2010 | Zhang et al. | 606/323 |
| 7,699,893 B2 * | 4/2010 | Donnelly et al. | 623/13.14 |
| 7,749,250 B2 * | 7/2010 | Stone et al. | 606/232 |
| 7,879,094 B2 * | 2/2011 | Baird et al. | 623/13.14 |
| 2009/0234451 A1 * | 9/2009 | Manderson | 623/13.14 |
| 2009/0248068 A1 * | 10/2009 | Lombardo et al. | 606/232 |
| 2009/0319043 A1 * | 12/2009 | McDevitt et al. | 623/13.14 |
| 2010/0082103 A1 * | 4/2010 | Blunn et al. | 623/13.14 |
| 2010/0100182 A1 * | 4/2010 | Barnes et al. | 623/13.14 |
| 2010/0121449 A1 * | 5/2010 | Sklar et al. | 623/13.14 |
| 2010/0161054 A1 * | 6/2010 | Park et al. | 623/13.14 |
| 2010/0161055 A1 * | 6/2010 | Donnelly et al. | 623/13.14 |
| 2010/0217389 A1 * | 8/2010 | Cheng et al. | 623/13.14 |
| 2010/0249929 A1 * | 9/2010 | Kurz et al. | 623/13.14 |
| 2010/0249930 A1 * | 9/2010 | Myers | 623/13.14 |
| 2010/0274355 A1 * | 10/2010 | McGuire et al. | 623/13.14 |
| 2010/0312341 A1 * | 12/2010 | Kaiser et al. | 623/13.14 |

FOREIGN PATENT DOCUMENTS

WO     WO9822047     5/1998

\* cited by examiner

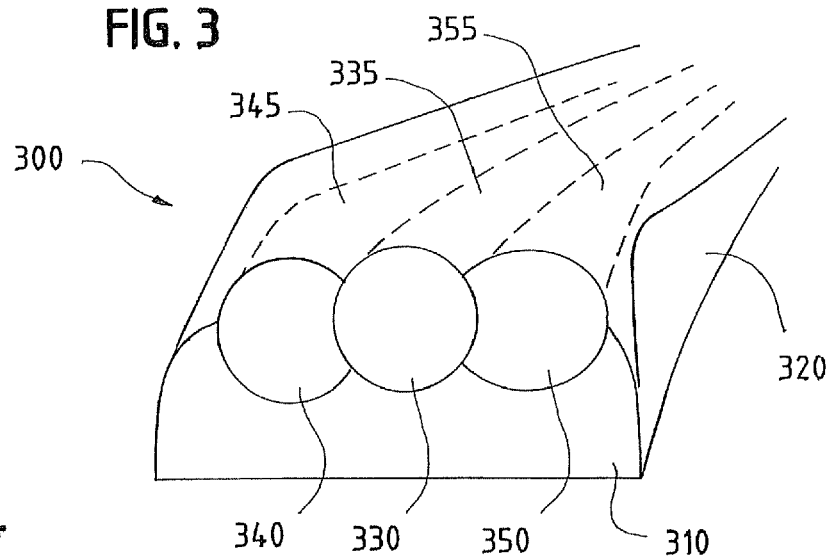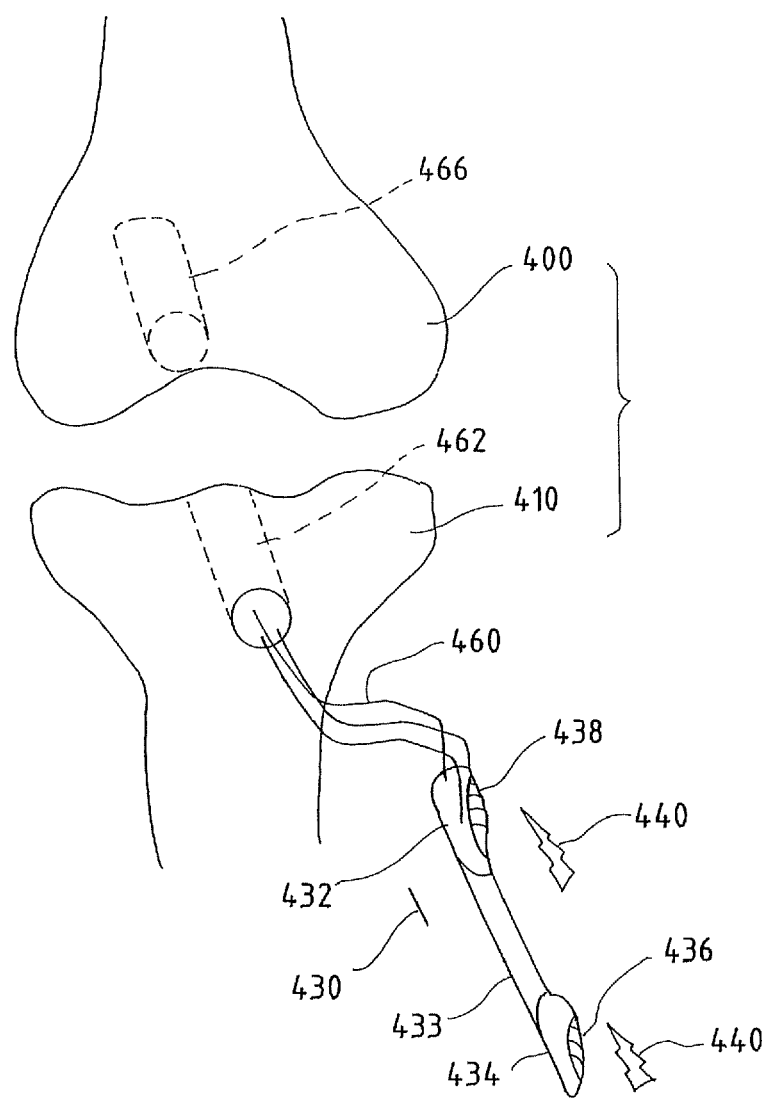

MATERIALS AND METHODS FOR IMPROVED BONE TENDON BONE TRANSPLANTATION

CROSS-REFERENCE TO RELATED APPLICATIONS

This application is a continuation of copending application Ser. No. 10/013,328, filed Nov. 5, 2001, which is a continuation in part of application Ser. No. 09/924,110, filed Aug. 7, 2000, now abandoned, which is a continuation in part of application Ser. No. 09/528,034, filed Mar. 17, 2000, now U.S. Pat. No. 6,805,713, which is a continuation in part of application Ser. No. 09/481,319, filed Jan. 11, 2000, now U.S. Pat. No. 6,497,726. The benefit of priority under 35 USC §120 is claimed for foregoing applications.

BACKGROUND OF THE INVENTION

Orthopedic medicine is increasingly becoming aware of the vast potential and advantages of using bone/tendon/bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting tendons to provide increased support to a damaged knee. These conventional techniques are not without their shortcomings; in most cases, the repaired joint lacks flexibility and stability.

The recent utilization of bone/tendon grafts has dramatically improved the results of joint repair in cases of severe trauma. Even in cases of extensive damage to the joint ligaments, orthopedic surgeons have been able to achieve 100 percent range of motion and stability using donor bone/tendon grafts.

Despite these realized advantages, there have been some difficulties encountered with utilizing bone/tendon grafts. For example, surgical procedures involving transplantation and fixation of these grafts can be tedious and lengthy. Currently, bone/tendon/bone grafts must be specifically shaped for the recipient during surgery, which can require thirty minutes to over an hour of time. Further, surgeons must establish a means of attaching the graft, which also takes up valuable surgery time.

Another difficulty associated with using bone/tendon grafts is that there is a limited supply and limited size range available. This can result in a patient having to choose an inferior procedure simply based on the lack of availability of tissue. Accordingly, there is a need in the art for a system that addresses this and the foregoing concerns.

SUMMARY OF THE INVENTION

The subject invention concerns a novel bone tendon bone graft (BTB) that facilitates an easier and more efficient surgery for reconstructing ligaments in a joint. One aspect of the subject invention pertains to a BTB that comprises a tendon and two bone blocks positioned at opposite ends of the tendon, wherein the bone blocks are pre-shaped for uniform and consistent alignment into a recipient bone.

In a specific aspect, the subject invention pertains to a bone tendon bone graft useful in orthopedic surgery comprising one or more bone blocks, and a tendon attached to said one or more bone blocks; wherein said one or more bone blocks is cut to provide a groove sufficient to accommodate a fixation screw. Alternatively, the subject invention pertains to a bone tendon bone graft useful in orthopedic surgery comprising one or more bone blocks and a tendon attached to said one or more bone blocks, wherein said one or more bone blocks is pre-shaped into a dowel.

A further aspect of the subject invention pertains to a method of obtaining a plurality of bone tendon bone grafts comprising excising a first bone plug having attached thereto a tendon or ligament; and excising a second bone plug having attached thereto a tendon or ligament; wherein said first bone plug and said second bone plug are derived from contiguous bone stock and overlap such that excision of said first bone plug or said second bone plug fauns a groove in the bone plug that is excised subsequent to the other.

Another aspect of the subject invention pertains to a BTB that comprises a tendon and one bone block, wherein the tendon is looped around a bone to create a tendon, bone, tendon layer held in place with sutures, and having two trailing portions of the tendon available for fixation at a remote location. This embodiment takes advantage of the natural cyclic creep associated with tendon movement to balance opposing forces in a pulley type fashion. This can increase tissue strength while decreasing shear that may cause tissue failure.

In yet another aspect, the subject invention pertains to a method of conducting orthopedic surgery on a human or an animal comprising obtaining a bone tendon bone graft, said graft comprising a tendon or ligament having two ends, and one or more bone blocks attached to said tendon or ligament, wherein at least one of said one or more bone blocks has a groove suitable for accommodating a fixation screw.

An alternative aspect of the invention pertains to an implant comprising a bone block and a tendon, wherein the bone block comprises a groove for accommodating a fixation screw.

Yet a further aspect of the invention pertains to a BTB having one or more segments that may be assembled to create different sized bone blocks.

Yet a further aspect of this invention pertains to a BTB that permits use of different types of tendons for ACL and PCL repair.

Yet a further aspect of the subject invention pertains to a BTB core cutter for harvesting BTB grafts in accordance with the principles of the subject invention.

Further still, another aspect of the subject invention pertains to a BTB obtained from xenogenic sources. Preferred sources include, but are not limited to, porcine, bovine, goat and equine.

These and other advantageous aspects of the subject invention are described in further detail below.

DETAILED DESCRIPTION OF THE DRAWINGS

FIG. 3 depicts a frontal view of a donor area for harvesting BTBs in accordance with the teachings herein.

FIG. 4 is a depiction of another embodiment of the invention illustrating a reconstruction of an injured area through implantation of a BTB in accordance with the teachings herein.

Figure 9A:
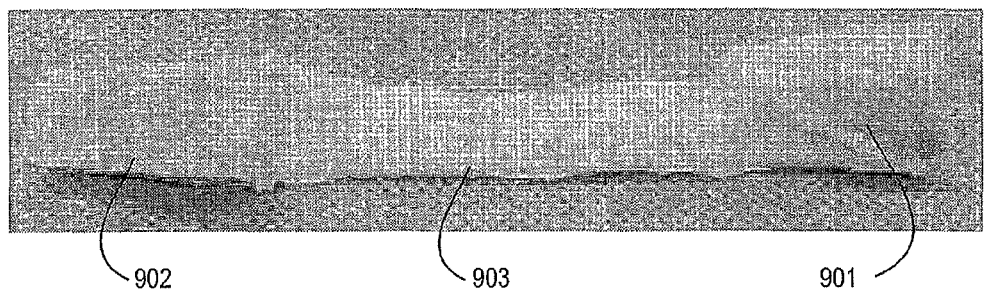

FIG. 9A is a photograph showing the posterior side of a single porcine Bone Tendon Bone graft traditionally cut and not pre-shaped. The longer bone is the tibia and the shorter bone is the patella. The tendon is also shown.

Figure 9B:
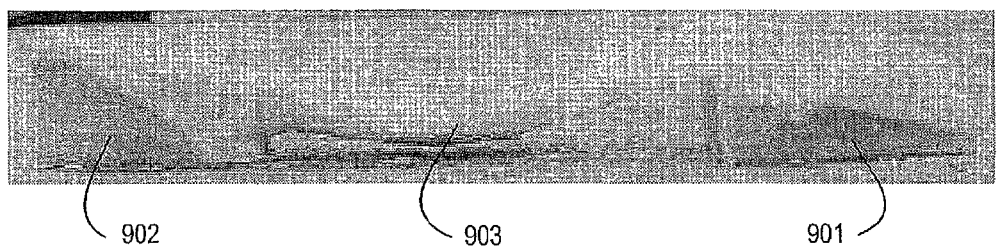

FIG. 9B is a photgraph showing the anterior view of the porcine BIB shown in FIG. 9A. The tibia is on the left and the patella is on the right.

Figure 9C:
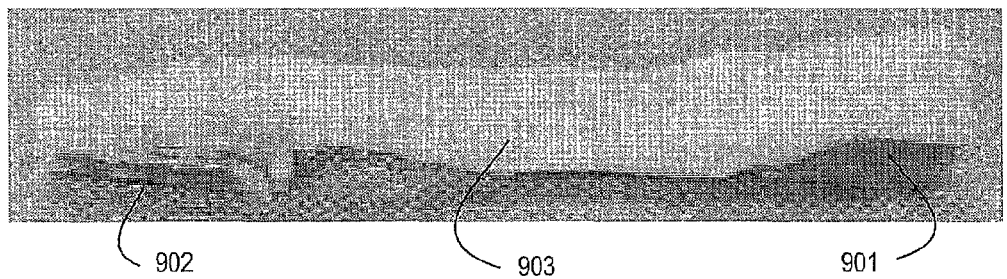

FIG. 9C is a side view of the porcine BTB shown in FIG. 9A to show the thickness of the tendon. The patella is shown on the left and the tendon is shown on the right.

Figure 10A:
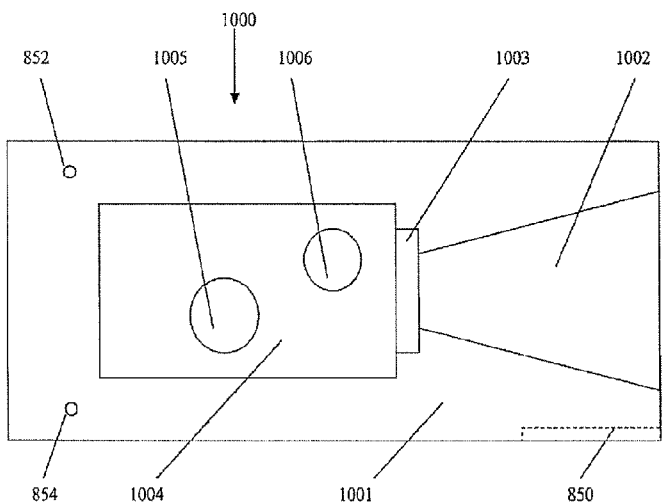

FIG. 10A is a side cross-sectional view of Looped Locking Assembled bone-tendon-bone block having a solid exterior surface and one or more interior chambers, graft manipulation holes 852 and 854, and an exterior groove 850 sufficient to accommodate a fixation screw.

Figure 10B:
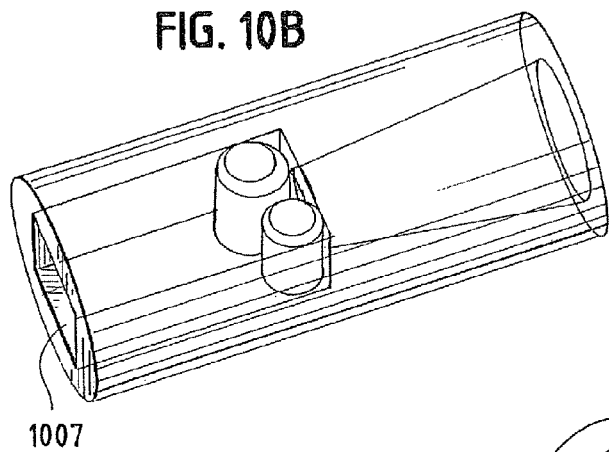

FIG. 10B is a three dimensional side view of a solid Looped Locking Assembled BTB bone block showing a distal opening into a distal interior fixation chamber.

Figure 10C:
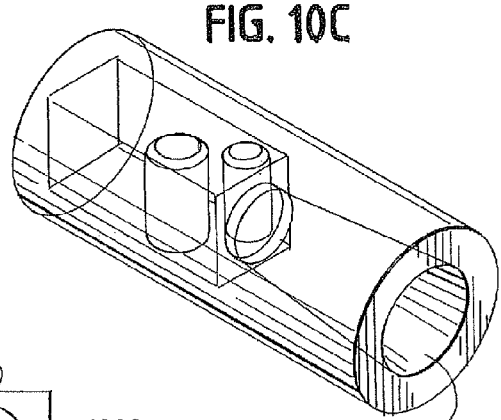

FIG. 10C is a three dimensional side view of a solid Looped Locking Assembled BTB bone block showing a proximal opening into a proximal interior 30 receiving chamber.

Figure 10D:
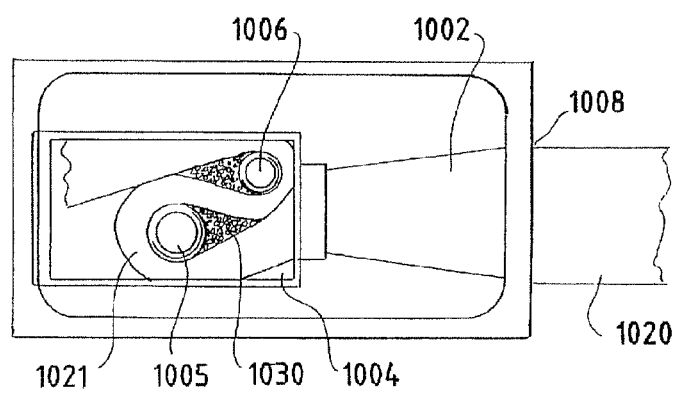

FIG. 10D is a side cross-sectional view of a solid Looped. Locking Assembled BTB bone block with tendon inserted.

Figure 11A:
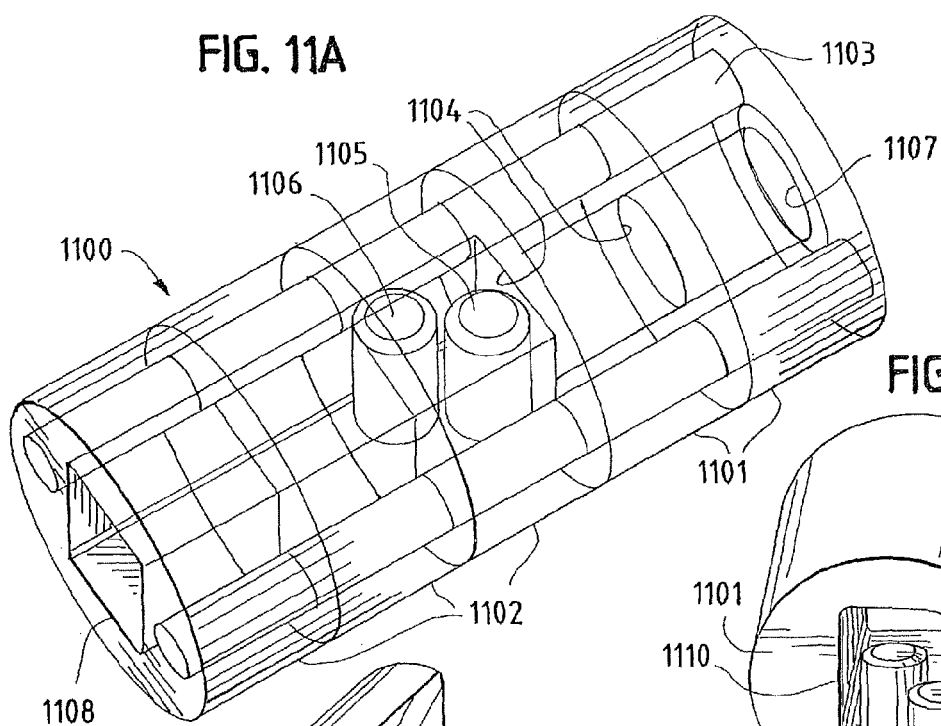

FIG. 11A is a three dimensional view of a segmented Looped Locking Assembled BTB bone block.

Figure 11B:
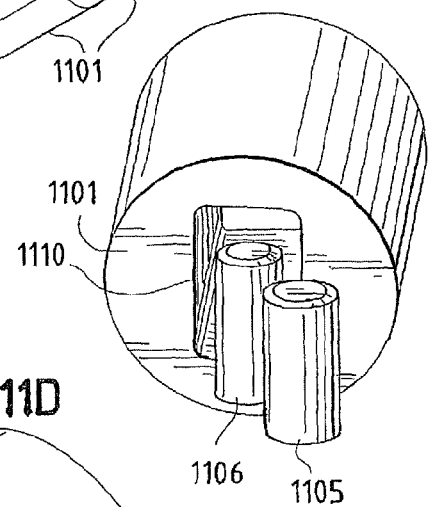

FIG. 11B is a view of one section of a segmented Looped Locking Assembled BTB bone block showing first and second fasteners.

Figure 11C:
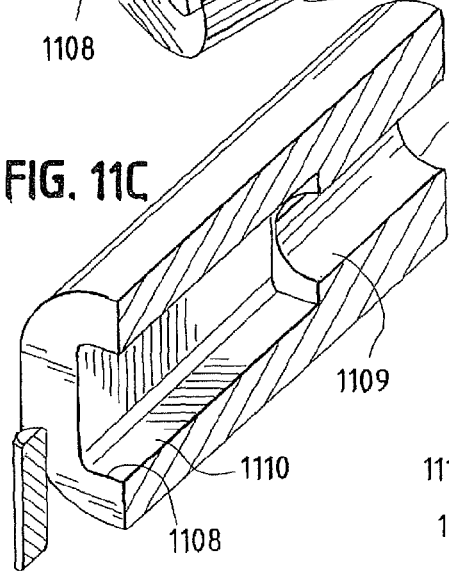

FIG. 11C is one half of a segmented Looped Locking Assembled BTB bone block cut longitudinally to reveal contours interior fixation and receiving chambers.

Figure 11D:
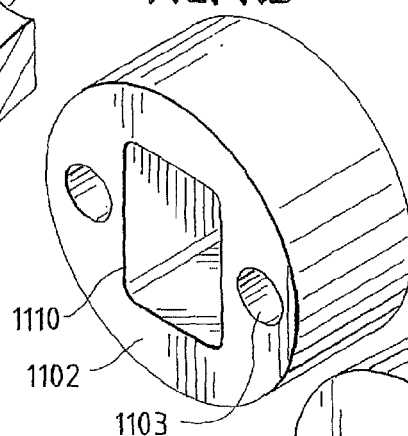

FIG. 11D is a distal section of a segmented Looped Locking Assembled BTB bone block showing rectangular opening of distal fixation chamber and holes for pins.

Figure 11E:
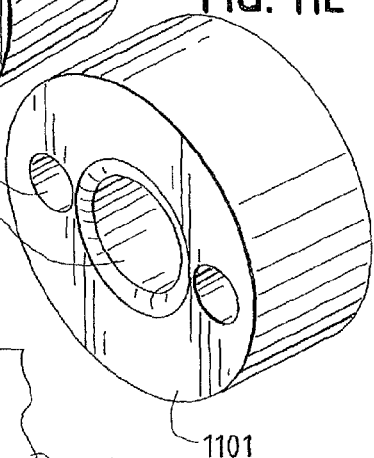

FIG. 11E is one proximal section of a segmented Looped Locking Assembled BTB bone block showing a circular opening for receipt of a tendon and holes for pins.

Figure 11F:
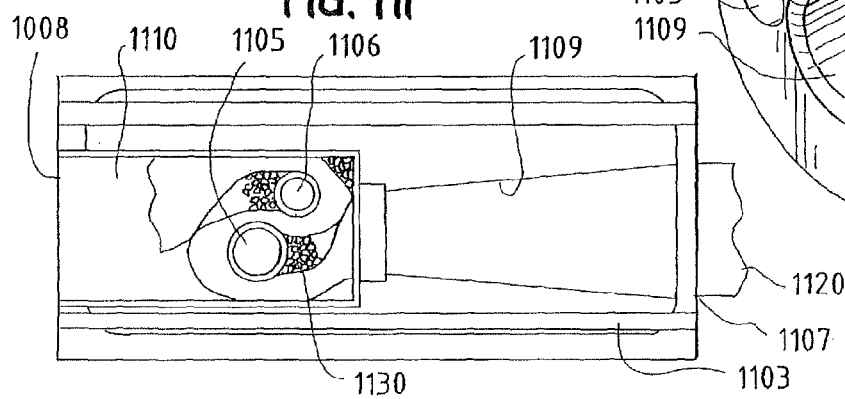

FIG. 11F is a side cross-sectional view of a segmented Looped Locking Assembled BTB bone block with tendon inserted.

Figure 12A:
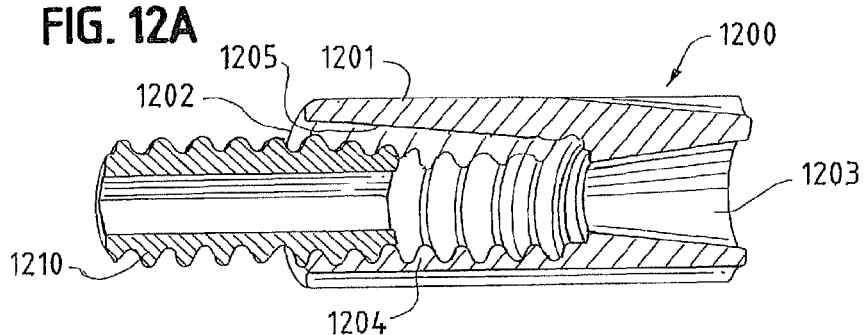

FIG. 12A shows a side cross-sectional view of a Solid Screw Wedge Assembled BTB bone block with modified interference screw partially inserted.

Figure 12B:
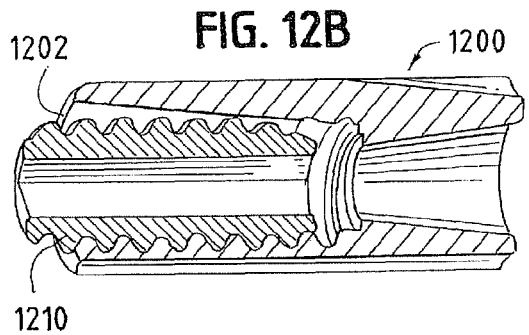

FIG. 12B shows a side cross-sectional view of a Solid Screw Wedge Assembled BTB bone block showing partially a threaded portion and a smooth portion of the distal chamber.

Figure 12C:
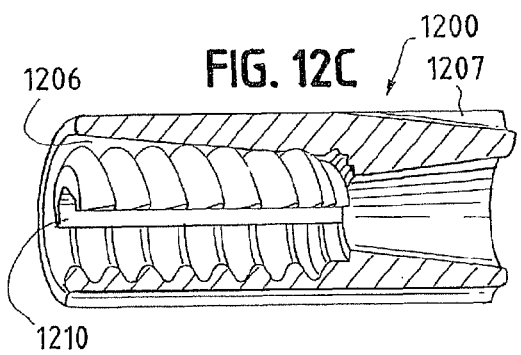

FIG. 12C is a side cross-sectional view of a Solid Screw Wedge Assembled BTB bone block with the screw completely threaded into cavity and showing gap between the block and the screw.

Figure 12D:
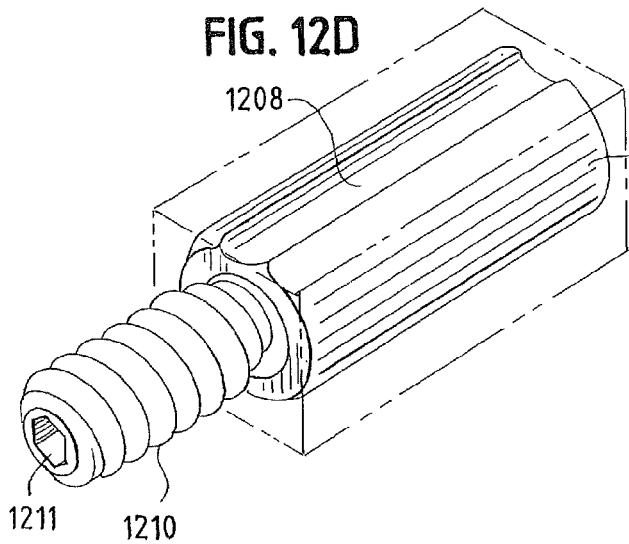

FIG. 12D is a side view of Solid Screw Wedge Assembled BTB bone block with the screw completely out showing a screw head shaped for ratcheting.

Figure 12E:
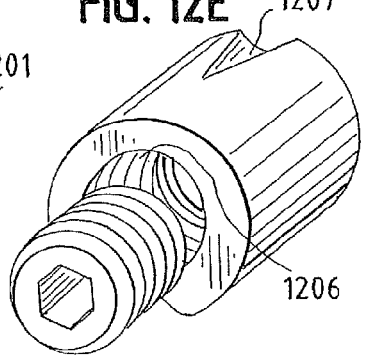

FIG. 12E is an angled front view of the Solid Screw Wedge Assembled BTB bone block with a screw completely out and showing the space between the screw and the block created by the inclined plane.

Figure 12F:
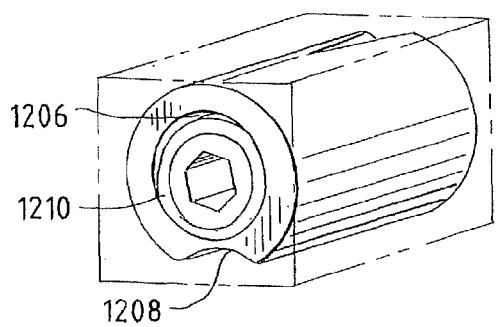

FIG. 12F is an angled front view of the Solid Screw Wedge Assembled BTB 30 bone block with a screw inserted showing space between screw and block created by inclined plane.

Figure 12G:
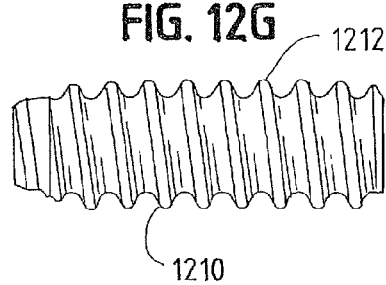

FIG. 12G is a side view of the screw used in the Solid Screw Wedge Assembled BTB bone block showing the smooth edges.

Figure 13A:
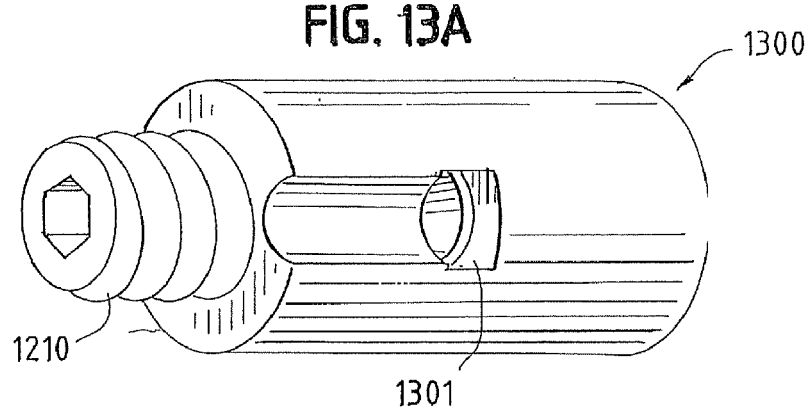

FIG. 13A is side view of a Solid Screw Wedge Assembled BTB bone block having a ported window not blocked by a screw.

Figure 13B:
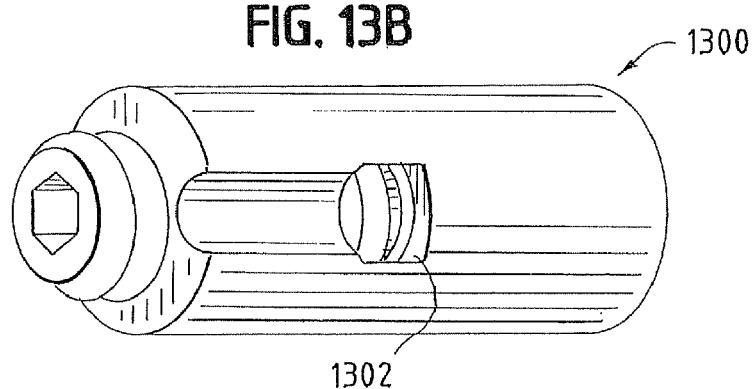

FIG. 13B is side view of a Solid Screw Wedge Assembled BTB bone block having a ported window partially blocked by a screw.

Figure 13C:
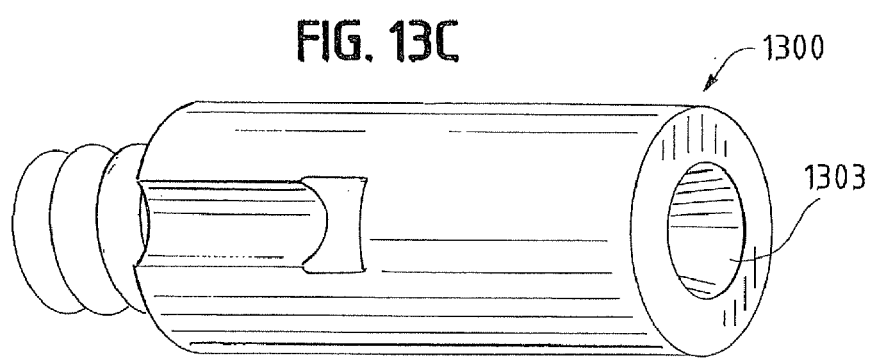

FIG. 13C is an angled side view of a Solid Screw Wedge Assembled BTB bone block showing an orifice to receive a tendon.

Figure 14A:
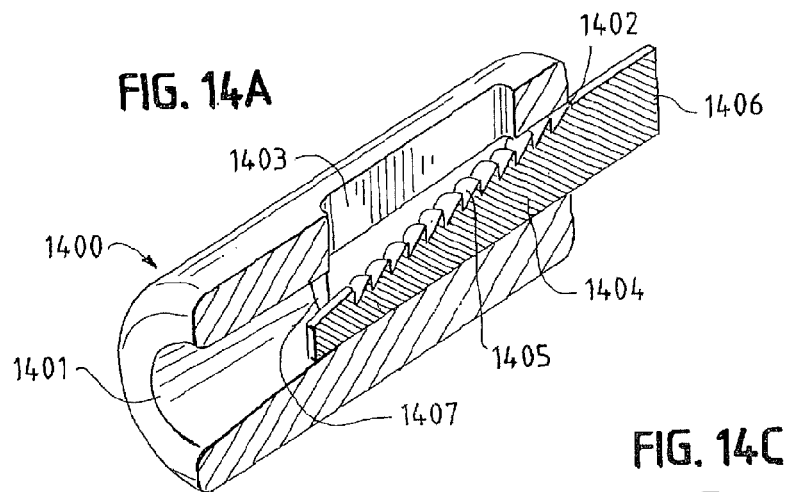

FIG. 14A is a three dimensional cross-sectional view of a Key Wedge 10 Assembled BTB bone block showing the key in an unlocked position.

Figure 14B:
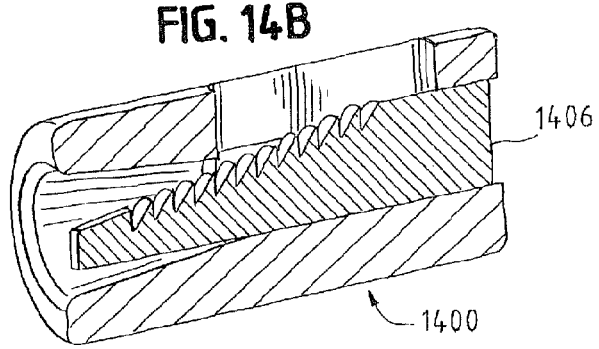

FIG. 14B is a three dimensional cross-sectional view of a Key Wedge Assembled BTB bone block showing the key in a locked position.

Figure 14C:
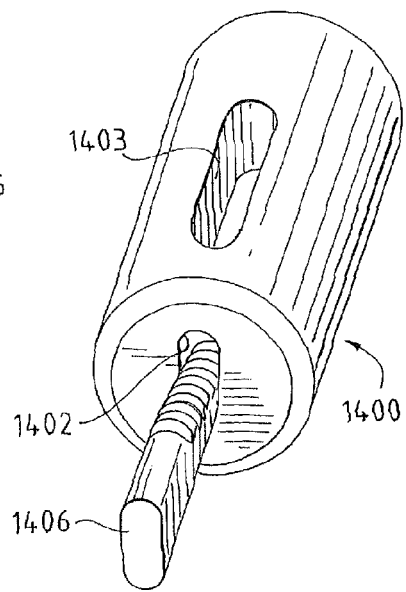

FIG. 14C is a three dimensional front view of a Key Wedge Assembled BTB bone block showing the key in the unlocked position and unobstructed ported window.

Figure 14E:
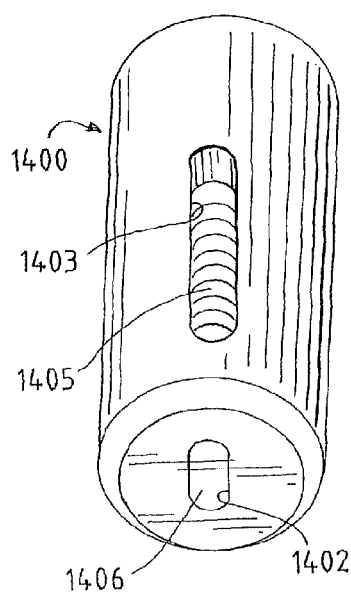
Figure 14D:
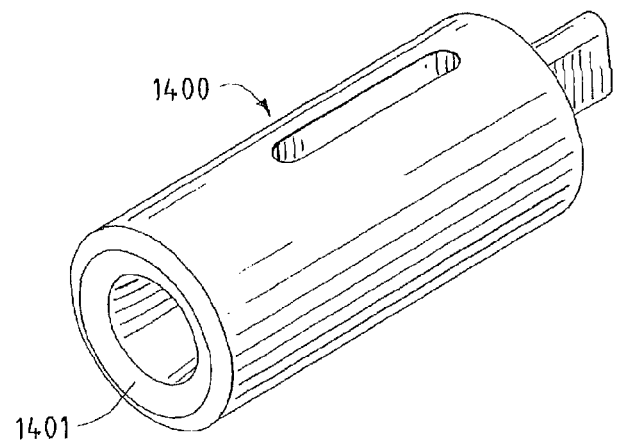

FIG. 14D is an angled front view of a Key Wedge Assembled BTB bone block showing an orifice to receive a tendon.

FIG. 14E is an angled front view of a Key Wedge Assembled BTB bone block with the key in a locked position and a partially obstructed ported window.

Figure 15A:
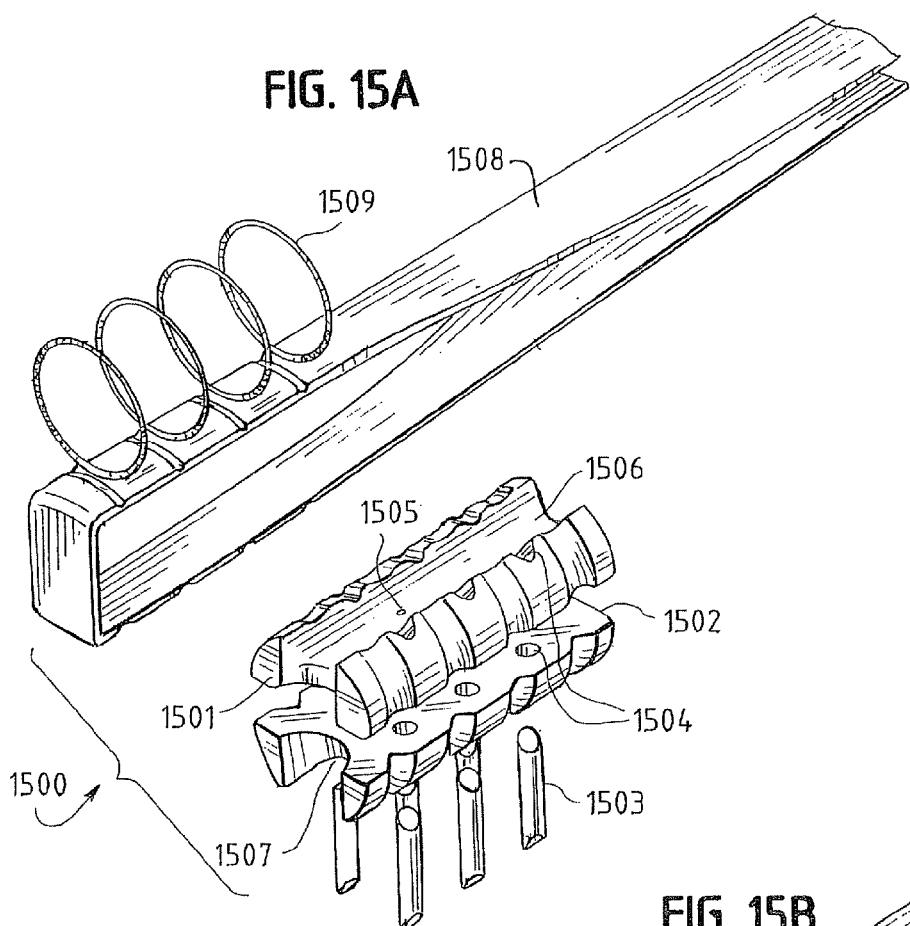

FIG. 15A is an exploded view of an assembled segmented looped pulley bone tendon showing all component parts including solid sutures.

Figure 15B:
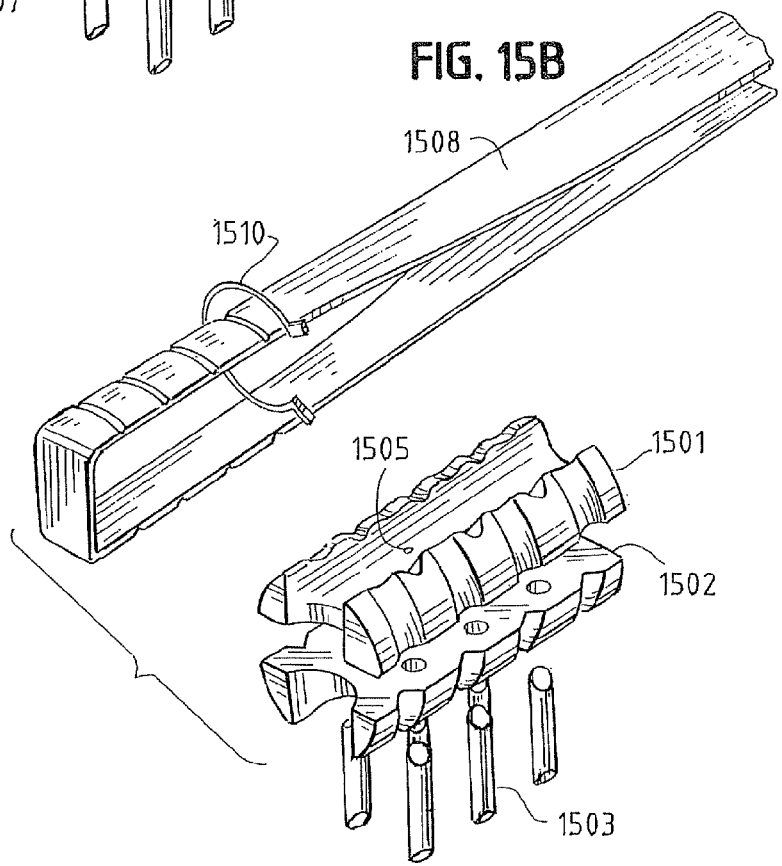

FIG. 15B is an exploded view of an assembled segmented looped pulley bone tendon showing all component parts including an open sutures.

Figure 15C:
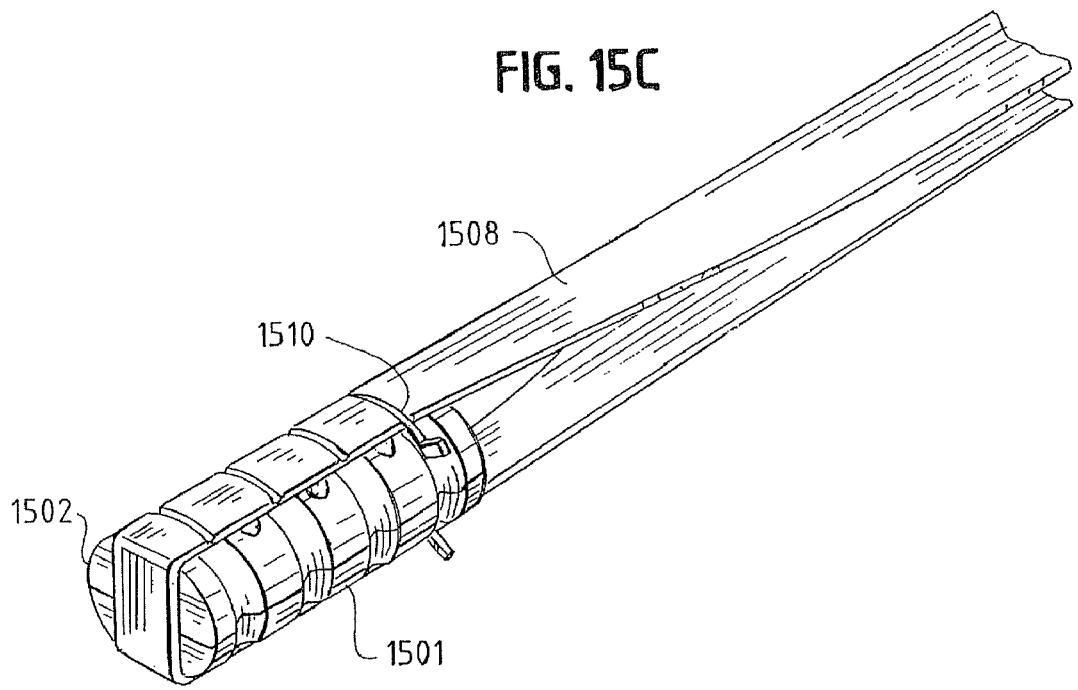

FIG. 15C shows an assembled segmented looped pulley bone tendon having an open suture design.

Figure 15D:
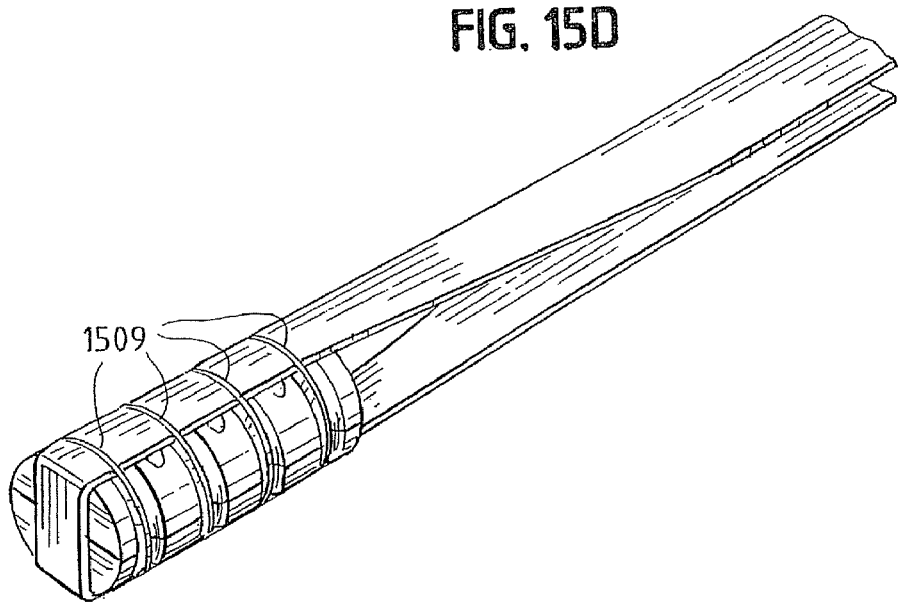

FIG. 15D shows an assembled segmented looped pulley bone tendon having an closed suture design.

DETAILED DESCRIPTION OF THE INVENTION

The present invention is directed to an assembled bone-tendon-bone graft useful in orthopedic surgery comprising one or more assembled blocks and a tendon affixed to said one or more assembled blocks. The one or more blocks comprise segments of cortical bone, cancellous bone, cortico-cancellous bone, or combinations thereof, wherein said bone segments are mineralized or partially or fully demineralized; or wherein said one or more blocks comprise segments of a synthetic material; or combinations of bone and synthetic material. It is also within the scope of the present invention that the tendon is derived from an Achilles tendon, patellar tendon, or quadriceps tendon of a donor, or other tendon or ligament from a donor, or is comprised of a synthetic material.

The synthetic material that is used in any synthetic segment of the assembled bone tendon bone graft is selected from the group consisting of stainless steel, titanium, cobalt chromium-molybdenum alloy, and a plastic. The plastic is one or more members selected from the group consisting of nylon, polycarbonate, polypropylene, polyacetal, polyethylene oxide and its copolymers, polyvinylpyrolidone, polyacrylates, polyesters, polysulfone, polylactide, poly(L-lactide) (PLLA), poly(D,L-lactide) (PLA), poly(glycolide) (PGA), poly(L-lactide-co-D,L-Lactide) (PLLA/PLA), poly(L-lactide-co-glycolide) (PLA/PGA), poly(glocolide-co-trimethylene carbonate) (PGA/PTMC), polydioxanone (PDS), polycaprolactone (PCL), polyhydroxybutyrate (PHBT), poly (phosphazenes), poly(D,L-lactide-co-caprolactone) (PLA/PCL), poly(glycolide-co-caprolactone) (PGA/PCL), poly(phosphase ester), polyanhydrides, polyvinyl alcohol, hydrophilic polyurethanes, and a combination of one or more bioabsorbable polymers.

Figure 1:
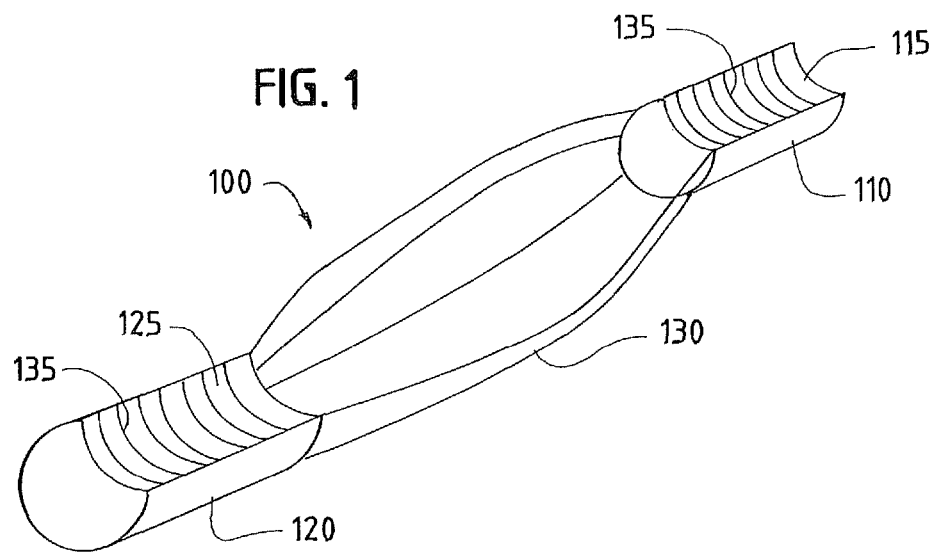
FIG. 1 shows an embodiment of a BTB having a groove with a thread profile disposed thereon.

Referring to FIG. 1, there is shown an embodiment directed to a BTB 100 comprising a first bone block 110 and a second bone block 120 interconnected by a tendon 130, wherein each bone block has been pre-shaped into dowels. The term "tendon" as used herein is intended in its broad sense and refers to fibrous connective tissue for use in grafts, such as, but not limited to, tendons, ligaments and demineralized bone. The terms "BTB" or "bone tendon bone graft" as used herein refer to a graft implant that comprises one or more tendon portions and one or more bone portions. The BTB is preferably isolated from the knee of a donor. However, in view of the teachings herein, those skilled in the art will readily appreciate that other areas of the body are suitable, albeit less preferred, for harvesting BTBs according to the subject invention, such as, but not limited to, the Achilles tendon/calcaneus region or shoulder region. In addition to BTBs to having a tendon portion derived from naturally occurring tendon or ligament harvested from a donor, other examples of suitable implants would be readily appreciated by those skilled in the art, such as, but not limited to, segmentally demineralized bone (International Pub. No. WO/99/21515). In a more preferred embodiment, one of the bone blocks is derived from the patella while the other is derived from the end of the tibia, and the tendon is derived from the patellar tendon.

To facilitate placement of a fixation screw, the dowels are preferably machined down the length of the bone block to form radius cuts 115, 125. The radius cuts 115, 125 aid in the attachment of the graft to recipient bone because they provide a groove to position a fixation screw, which results in increased surface area at the contact between the bone block and the screw. The radius cuts 115, 125 provide the additional advantage of increasing the pull out loads of the bone block, as well as filling of "dead" space in the tunnel.

Fixation methods known in the art can be used in accord with the principles of the subject invention, which include, but are not limited to, staples, buttons, screw and washer, interference screws, and self-taping screws. In a preferred embodiment, fixation is accomplished by interference screws and/or self-taping screws. In an even more preferred embodiment, the radius cuts 115, 125 contain a thread profile 135 that matches the thread profile of the fixation screw, thereby further increasing the stability of fixation.

Figure 2A:
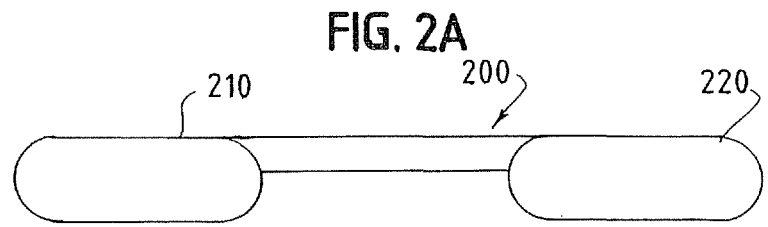
FIG. 2 shows a side view of three different embodiments of BTBs in accordance with the subject invention.
Figure 2B:
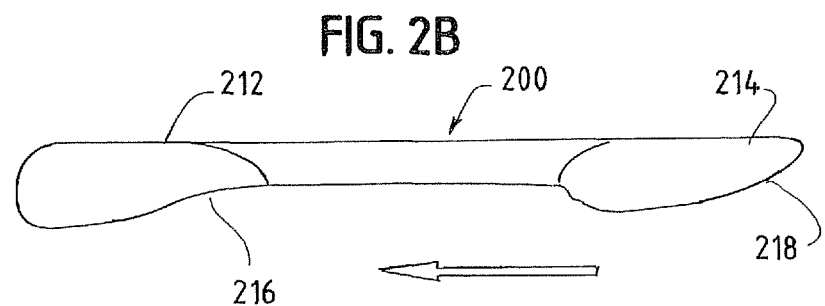
Figure 2C:
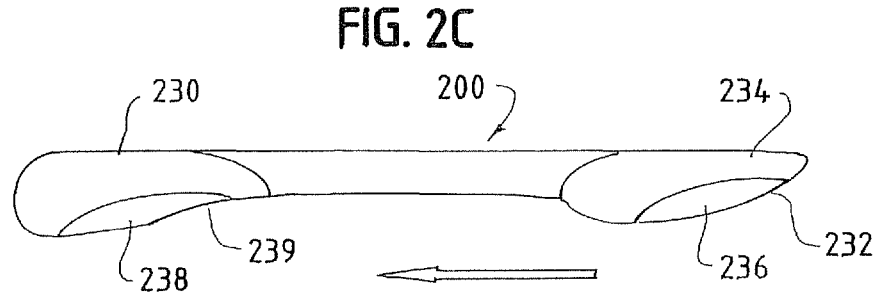

Referring now to FIG. 2, three different embodiments of the subject BTBs are shown. FIG. 2A shows an embodiment that comprises a basic configuration of the subject BTBs. Bone blocks 210 and 220 are in a pre-shaped dowel form with no groove thereon, and are connected by tendon 100. FIG. 2B shows another version of the BTB, wherein the bone blocks are pre-shaped into dowels with tapered ends. Bone block 212 is a dowel that has a proximal tapered region 216 in relation to tendon 200, and bone block 214 is pre-shaped into a dowel that has a distal tapered region 218 in relation to tendon 200. FIG. 2C illustrates a preferred version of the invention, which has a bone block 230 with a proximal tapered region 239 and a groove 238 positioned on the bone block 230. This version also comprises a second bone block 234 with a distal tapered region and a groove 236 positioned on bone block 234 as well. The embodiments shown in FIGS. 2B-C are tapered such that implantation into a pre-formed tunnel in recipient to bone is preferred to occur in the direction of the arrow (see also FIG. 4).

Referring to FIG. 3, an illustration of a donor area 300 is depicted, wherein three separate grafts 335, 345, and 355 are harvested. As shown, the three different grafts individually have at least one bone block 330, 340, and 350. While the sequence of harvesting the grafts is not critical, preferably, graft 335 is excised first, followed by excision of the outside grafts 345, 355. Excising graft 335 first results in the automatic cut in the other donor areas, thereby producing a groove in the bone blocks 340, 350 of the other grafts upon excision. In a preferred embodiment, the donor area is located at the top of the Tibia at the insertion of the patellar tendon 320. In an even more preferred embodiment, the donor area extends the length of the patellar tendon to the patella, wherein bone blocks are excised from the patella.

The bone blocks can be extracted with the use of conventional tools and protocols routinely practiced in the art, such as core cutter and hole saws. In a preferred embodiment, the bone blocks can be extracted through the use of a BTB bone cutter according to the teachings further described below.

The extracted bone blocks 330, 340, and 350 are generally shaped like a plug or dowel and are preferably further shaped by machining through conventional methods known in the art. In a specific embodiment the dowel is machined into dimensions suitable for various surgical procedures. The machining is preferably conducted on a graduated die, a grinding wheel, a lathe, or machining tools may be specifically designed and adapted for this purpose in view of the teachings herein. Preferred dimensions for the dowels include 8 mm, 9 mm, 10 mm, 11 mm, and 12 mm in diameter. Reproducibility of the product dimensions is an important feature for the successful use of such grafts in the clinical setting.

In a specific embodiment, the subject invention is directed to a method of repairing an injured cruciate ligament in the knee involving the implantation of a BTB. FIG. 4 illustrates this procedure, and shows a femur 400 and tibia 410 having tunnels formed therein, 466 and 462, respectively, for receiving BTB 430, which comprises two bone blocks 432 and 434 connected by tendon 433. To aid in guiding the BTB 430 through tunnel 462, sutures 460 are optionally engaged to bone block 432, which allow a surgeon to pull the BTB 430 through tunnel 462 where the sutures 460 can then be removed. Once the BTB 430 is properly situated in tunnels 462 and 466, the BTB 430 is secured in the recipient bone by interference screws 440. The interference screws 440 are preferably self taping and are engaged by rotation in the space between grooves 438 and 436 and the inner walls of tunnels 466 and 462, respectively. In an even more preferred embodiment, the BTB can be pre-marked with alignment markings. Such markings can be positioned on the BTB to aid the surgeon in visualizing the depth of the BTB in the tunnels fowled for receiving the BTB, as well as visualizing bone ligament junctions and rotation of the BTB.

Figure 5:
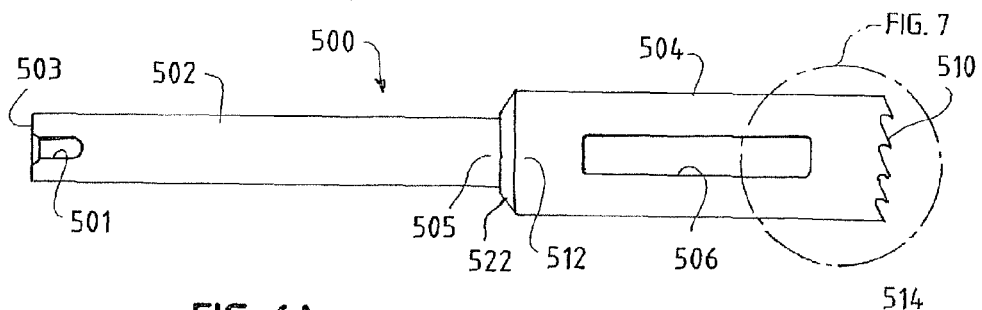
FIG. 5 shows a side view of a BTB core cutter of the subject invention designed for harvesting BTB grafts.
Figure 6A:
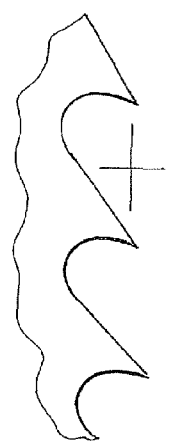
FIG. 6A shows a close up view of a teeth configuration that is less desired for use with the subject invention.
Figure 6B:
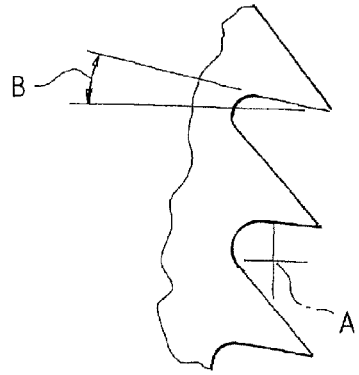
FIG. 6B shows a close up view of a preferred embodiment of the teeth of the embodiment shown in FIG. 5.
Figure 7:
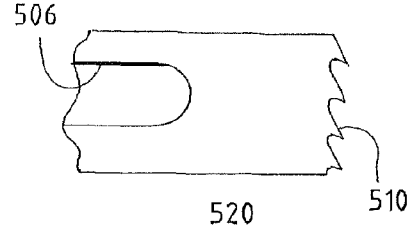
FIG. 7 is a blown up view of the circled region as shown in FIG. 5.

Referring now to FIGS. 5-7, another embodiment of the subject invention is shown that is directed to a BTB harvesting device, such as core cutter 500 that comprises a shaft 502 having a first end 503 and a second end 505. The first end 503 of the shaft 502 preferably has a cavity 501 longitudinally disposed thereon, which is designed for engaging a drill, such as by insertion of a Jacob's chuck attached to a power drill (e.g., Dupuy). The second end 505 of the shaft 502 can be attached to a first end 512 of a hollow cylinder 504. The second end 514 of the cylinder 504 preferably has teeth 510 disposed thereon. In a preferred embodiment the cylinder has at least one slot 506 disposed on its surface to aid in the removal of the cut graft tissue from the core cutter 500. The slot 506 also provides a means to wash the graft during the extraction procedure to thereby decrease the chance of frictional burning of the graft. In a preferred embodiment, the shaft 502 is approximately 90 mm in length, the cylinder 504 is approximately 50 mm in length, and the slot 506 is approximately 30 mm in length. In an even more preferred embodiment, the first end of the hollow cylinder 512 has a chamfered portion 522 which angles down to the shaft 502.

A blown up view of the core cutter teeth 510 is illustrated in FIG. 6. It is preferred that the radius of the teeth A and rake angle of the teeth B (also referred to as a bottom angle) are of appropriate values as to avoid failure (e.g. bending or breaking) of the teeth, as well as undesired damage to the graft. For example, FIG. 6A shows an unacceptable tooth pattern wherein the radius A and bottom angle B are too large, resulting in insufficient support structure for the tooth and inevitable failure. According to the subject invention, a core cutter having a diameter of approximately 10-11 mm preferably has approximately 14 teeth, with a tooth radius A of approximately 20-30 mm (25 mm being more preferred) and a bottom angle B of approximately 10-20 degrees (15 degrees being more preferred). For core cutters designed for smaller or larger bone blocks, the foregoing dimensions are preferably maintained, while the number of teeth are appropriately decreased or increased. In a preferred embodiment, the number of teeth are decreased or increased by two for every millimeter below or above, respectively, the 10-11 mm cylinder diameter. For example, a core cutter having a 12 mm cylinder diameter would preferably have about 16 teeth.

A blown up view of an end section (circle shown in FIG. 5) of the cylinder 504, is shown in FIG. 7, which illustrates a preferred embodiment of the cylinder 504 wherein the internal diameter (ID) is decreased slightly by adding a relief thickness 520 to the inner surface of the cylinder 504. This embodiment provides an additional convenience when using a size gauging device (e.g. ring) for selecting extracted bone blocks that are within desired parameters. For example, the selection of a BTB through a 10 mm sized gauging device would preferably require the BTB to be a slight fraction smaller in diameter than the gauging device, otherwise any insignificant irregularity in the shape of the BTB might cause it to fail to pass through the gauging device. The relief thickness 520 decreases the ID of the cylinder 504, thereby effectuating this slight modification to the BTB.

Figure 8:
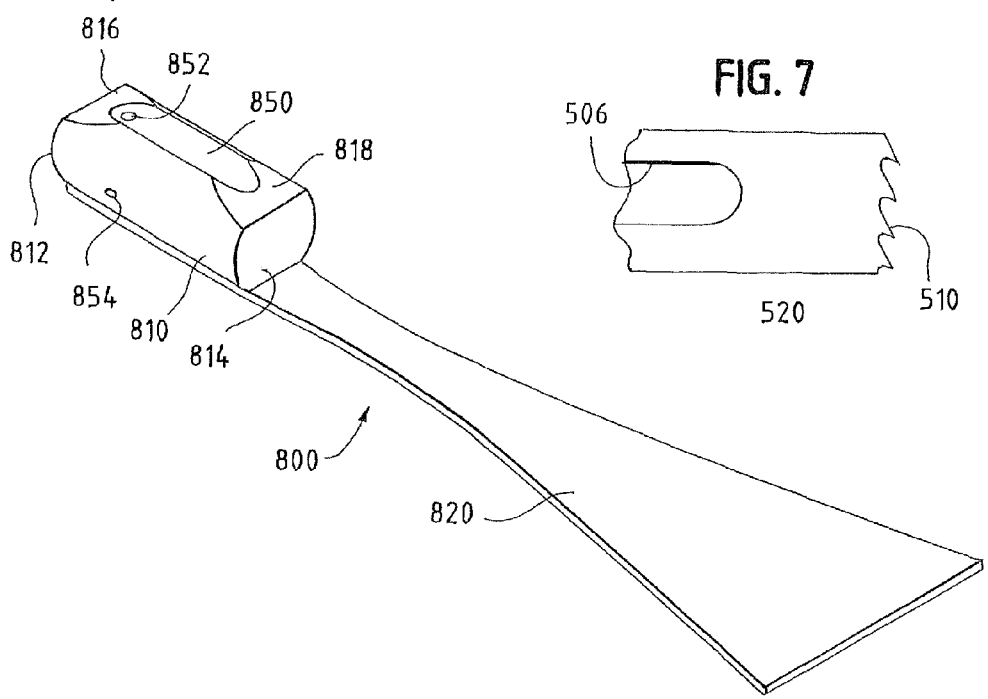
FIG. 8 is three dimensional side view of a further embodiment of the subject BTB that comprises one block that is tapered on both ends.

Shown in FIG. 8 is a further embodiment 800 of the subject BTB that is especially adapted for implantation during knee surgery, wherein the implantation and securement of the BTB is bi-directional. BTB embodiment 800 comprises one bone block portion 810 and one tendon portion 820. A preferred area from which embodiment 800 is harvested would be the heel, thigh, or shoulder. More preferably, the area from which embodiment 800 is harvested is the heel or thigh, whereby tendon portion 820 is derived from an Achilles tendon or quadriceps tendon of a donor. The bone block portion 810 comprises two ends 812 and 814 which both comprise a tapered region 816 and 818, respectively. The presence of the two tapered regions 812 and 814 allows for the BTB embodiment 800 to be inserted and secured bi-directionally, which means, for example, implantation in either the tibial 462 or femoral 466 tunnels as discussed above in reference to the method diagrammed in FIG. 4. Of course, the site of implantation could be approached from a superior point of entry, i.e., establishing a through-tunnel in the femur as opposed to the tibia; BTB embodiment 800 would be suitable for securement in either tunnels in such alternative procedure as well. Further, the bone block 810 can be provided with a groove 850 to aid in the securement of the implant. In addition, during implantation, it may be desirable to have a means for manipulating the implant, such as by sutures or graft insertion tools. Accordingly, BTB embodiment 800 is provided with preformed graft manipulation holes 852 and 854 for receiving a suture and/or graft insertion tools. By way of example of illustrating the orientation of the graft manipulation holes, holes 852 and 854 are shown as being vertical or horizontal, respectively, to the axis of the bone block 810. The preformed graft manipulation holes can be made by conventional methods, such as by drilling. Appropriate tools for insertion into preformed holes 852 and 854 will easily be appreciated by those skilled in the art. Preferably, the graft insertion tool(s) used comprise an end having a shape and size suitable for insertion into the graft manipulation holes.

A BTB obtained from a pig knee according to the disclosed method is shown in FIGS. 9A, 9B and 9C. The BTB is traditionally cut and not pre-shaped. FIG. 9A shows a posterior view of the BTB graft generally indicated at 900 comprising a section of tibia bone 901 bone, and a section of patella bone 902 connected together by a patella tendon 903. FIG. 9B shows the same graft from an anterior perspective showing the tibia bone 901, patella bone 902 and tendon 903. FIG. 9C is a picture of the BTB of FIG. 9A from the side to demonstrate the thickness of the tendon 903 between the tibia bone 901 and patella bone 902.

In alternate embodiments assembled bone blocks for use in BTB's is presented. FIG. 10A shows a side cross sectional view of a Looped Locking Buckle assembled BTB bone block generally represented at 1000. The block has solid exterior 1001 and an interior having multiple compartments to accommodate and hold in place a tendon placed therein. An interior receiving chamber 1002 funnels down to an interior fixation chamber opening 1003 leading to an interior fixation chamber 1004. A first fastener device 1005 and a second fastener device 1006 are situated such that one of the fasteners is fixed longitudinally and laterally while the other fastener is allowed to rock over it. Preferably each fastener device is a dowel shaped roller with one dowel being larger that the other. Ideally the smaller fastener has a diameter of approximately 2.7 mm and a length of approximately 6 mm, while the larger fastener has a diameter of approximately 3.3 mm and a length of approximately 6 mm. The size of the fasteners may vary depending upon the particular application and dimensions of the bone block. FIG. shows a "look through" view of the bone block taken from the side to show all components in three dimensions and showing a distal opening 1007 that allows access to said tendon when placing it over the fastener. FIG. 10C is an angled front "look through" view in three dimensions showing a proximal opening 1008 for insertion of a tendon or other tissue. FIG. 10D shows a side cross-sectional view of the bone block with a tendon retained therein. A tendon 1020 is inserted into the proximal opening of the bone block, and into a receiving chamber 1002 and into the interior fixation chamber 1004. The tendon is squeezed down to a smaller diameter and then spread flatly around a first fastener device 1005 and then around a second fastener device 1006. One of the fasteners devices is fixed longitudinally and laterally while the other is allowed to rock over it. Because the fixation devices are of different sizes, at the point of highest tension, the fixation devices create a cam over-locking arrangement to hold the tendon in place. It is also preferable to impregnate the tendon with small cancellous bone chips 1030. In another embodiment, the bone chips are particles of cortical bone, cancellous bone, cortico-cancellous bone or a combination thereof. The bone chips increase friction between said tendon and said first and second rollers to reduce tendon movement. Thus in one embodiment, the tendon impregnated with bone chips is inserted through the proximal receiving chamber and into the distal fixation chambers for fixation to said rollers. In this embodiment, the fixation of said tendon impregnated with bone chips comprises looping the tendon around the first and second rollers in opposite directions such that a cam over affect is achieved to lock the tendon in place between the rollers, and wherein the bone chips become positioned between the rollers and the tendon to increase friction between the rollers and the tendon thereby further restricting movement of the tendon. As the tendon is pulled, the bone chips pack around the tendon giving additional grip to the surface of the fastener device and become tiny breaks that help attach the tissue to the bone with frictional force. This solves the problem of slippage present in other BTB devices.

FIG. 11A shows a side "look through" three-dimensional view of a segmented Looped Locking Buckle Assembled BTB bone block generally represented at 1100. A series of machined proximal segments 1101 and distal segments 1102 are held in place by dowels 1103 that are stretch the length of the implant. The sections are put together to create a bone block that is structurally identical to the solid version described above in FIGS. 10A-D. Each proximal section 1101 and distal section 1102 has a hole 1104 machined therethrough, such that when joined together, a passageway is created for insertion and retention of a tendon. A tendon enters through the proximal opening 1107 and looped around first 1105 and second 1106 fastener devices in an identical fashion to that described above. A distal opening 1108 that allows access to the tendon from the distal side is also shown FIG. 11B shows one distal 1101 segment of a segmented bone block. The segment is machined to form a first section of a rectangular opening 1110 of an interior chamber containing a first fastener device 1105 and a second fastener device 1106. FIG. 11C shows one half of a segmented bone block. A proximal opening 1107 leads to an interior receiving chamber 1109. A distal opening 1108 leads to an internal fixation chamber 1110. FIG. 11D shows one section of a distal segment 1102 of the segmented bone block having a section of a rectangular opening 1110 cut therethrough and an opening 1103 for receipt of a dowel. FIG. 11E shows one section of a proximal segment 1101 of a segmented bone block having a circular opening cut therethrough and an opening for receipt of a dowel 1103. FIG. 11F shows a segmented bone block with tendon 1120 attached. The tendon 1120 enters through a proximal opening 1107 into a receiving chamber 1109 and then into a fixation chamber 1110 where it is looped around a first fastener device 1105 and then a second fastener device 1106 in a direction opposite to that used on the first fastener device. The tendon may be manipulated by accessing the distal opening 1108. To help retain the tendon, cancellous bone particles 1130 are coated onto the tendon such that through rolling over the fixation devices, the particles become positioned to act as brakes to the tendon. The individual segments are held in place by 1103 dowels running the length of the bone block.

The operation of this device is identical to that described for the solid bone block of FIGS. 10A-D, with the major difference being segmentation which allows for the production of larger grafts.

FIGS. 12A-F show cross-sectional views of an embodiment of a Solid Screw Wedge Assembled BTB bone block generally indicated at 1200. FIG. 12A shows a solid bone block 1201 having distal 1202 and proximal 1203 chambers. The distal chamber 1202 has a partially threaded segment 1204, and an unthreaded segment 1205 that is inclined and tapers away distally. A modified interference screw 1210 is used to retain a tendon placed into the bone block via the proximal chamber 1203. FIG. 12B shows a cross section of the Solid Screw Wedge Assembled BTB bone block with the screw 1210 threaded into the distal chamber 1202. FIG. 12C shows the screw 1210 completely screwed into the distal chamber and reveals a space 1206 between the screw and the wall of the bone block. In use, a portion of a tendon is threaded through the proximal end of the bone block and is fixed in place through insertion of the screw 1210. As the screw is inserted the terminal end of the tendon is forced against the distal wall of the bone block and held in place. A groove 1207 is formed on the exterior of the bone block to accommodate an interference screw during implantation. FIG. 12D shows a side view rotated to reveal a lengthwise ridge 1208 on the bone block 1201 that may accommodate an interference screw. As shown the modified interference screw 1210 has a pentagonal shaped depressed head 1211, which accommodate a socket device for ratcheting it into the bone block. FIG. 12E shows an angled front view of the same embodiment. FIG. 12F shows an angled front view with the screw 1210 inserted to reveal the space 1206 that accommodates a portion of a tendon and a lengthwise ridge 1208 which may accommodate an interference screw during implantation. FIG. 12G shows a side profile of the modified interference screw 1210 having smooth threads 1212. The solid screw wedge design offers the increased wedging capabilities of an inclined plane without significant wall loading. The smooth threads of the modified interference screw offers strength without the risk of tearing the tendon. The tendon is pulled into a partial threaded area and the screw is used to tighten the tendon to the side as well as anchoring it to the bottom using the interference screw's natural shape on its end to act as a socket head cap screw. The inclined plane of the screw has more mechanical advantage than the wedge, and the solid design lends itself to less lateral loading. The end of the modified interference screw has a cup like feature similar to a cup style set screw. The landing is smooth and should reduce tearing at that point. In this embodiment the wedge is eliminated and a rotary incline takes its place. Thus, the surgeon could pre-tighten the tendon to a desired torque. Loads are distributed evenly over the length of the dowel. The tendon is wedged and set when the screw is tightened.

FIGS. 13A-C shows a solid ported screw assembled BTB bone block. This embodiment is identical to that disclosed in FIGS. 12A-G, except that it has a ported window. FIG. 13A shows a side profile of a solid ported screw assembled BTB bone block generally depicted at 1300 having a modified interference screw 1210 partially threaded into the block. A ported window 1301 permits tissue contact with the formed canal. FIG. 13B shows a side profile of a solid ported screw assembled BTB bone block with the screw inserted to partially block the ported window. FIG. 13C shows an angled front view of the bone block showing a proximal opening 1302 into which a tendon is placed. This embodiment retains the features of the solid screw wedge assembled BTB described in FIGS. 12A-G, with the addition of a ported window that allows a portion of the tendon to contact the surgeons canal. The screw applies more pressure and has less chance of backing out. The inclined plane reduces the tendency to crack the wall under stress loading longitudinally. Further, the ported window allows tissue to extend the length of the dowel so as to contact the wall surface of the surgeon's canal allowing for better blood flow and attachment.

FIG. 14A is a side, cross-sectional view of a solid core Encapsulated Locking Key Wedge assembled BTB bone block generally indicated at 1400. The block is machined to have a proximal opening 1401 and distal opening 1402 and a ported window 1403. A tapered key 1404 is shown having saw toothed teeth 1405 along its top edge. The key decreases in height moving from its distal end 1406 towards its proximal end 1407. The saw tooth teeth are designed to grip the tendon and hold it in place. As shown, the bone block is in an unlocked position. FIG. 14B shows the bone block in a locked position.

FIG. 14C shows an angled top view of the bone block in an unlocked position. The distal end of the key extends beyond the distal opening 1402 leaving the ported window 1403 unobstructed. FIG. 14D shows an angled top view showing a proximal opening 1401 to receive a tendon. FIG. 14E shows a bone block in a locked position. The distal end 1406 of the key 1404 is flush with the distal opening 1402. The grooved teeth 1405 are shown filling a portion of the ported window 1403. In use, a tendon is inserted into the proximal opening and pushed toward the distal end. The key is moved in a proximal direction such that the teeth engage the tendon and hold it in place by pressing it against the interior walls. A portion of the tissue is then forced through the ported window to interact with the canal created by the surgeon. This interaction will result in better blood flow and faster attachment.

Previously used two sided wedges have caused splitting of the bone section of the assembly long before optimal loads were reaches. In this embodiment, the encapsulated key design places less exterior pressures on the dowel during loading. The key may function on its own, or using a drying process on the tendon, be kept under pressure until seated and then trimmed off. In the event the key slips, pre-loading and side pinning remain viable options. This solid design allows for longitudinal force transfer rather than lateral which will make it more difficult to crack.

FIGS. 15A-D show an assembled Segmented Looped Pulley bone tendon block. FIG. 15A shows a side profile exploded view of the bone tendon block. An upper bone block 1501 and a lower bone block 1502 are held together through insertion of press pins 1503 which are inserted through holes 1504 in both upper 1501 and lower 1502 bone blocks. The press pins are cortical bone, cancellous bone, cortico-cancellous bone or a combination thereof. Ideally, these press pins are 2 mm in length, but may vary depending upon specific needs. A pull hole 1505 is machined into the upper 1501 or lower 1502 bone block. The upper bone block is machined to have a depressed groove 1506 running the length of the bone block. The lower bone block 1502 is also machines to have depressed groove 1507 running the length of the bone block. A tendon 1508 and welded sutures 1509 are also shown. FIG. 15B shows the same picture, except that an open suture 1510 design replaces the welded suture 1509 design. FIG. 15C is an assembled view showing a tendon 1508 looped around an upper 1501 and lower 1502 bone block and held in place by an open suture. FIG. 15D is the same picture, except that the tendon is held in place by multiple welded sutures.

This embodiment is not a BTB, but a modified bone tendon for anterior cruciate ligament (ACL) or posterior cruciate ligament (PCL) repair that provides solutions to multiple problems encountered in these types of repairs. Traditional ACL or PCL repair techniques utilize a single semitendinosus which becomes prone to failure when connected by mechanical means to any one bone block. The reason for this is cyclic creep and fibril backbone breakdown which occurs due to the means of attachment which, in turn, disrupts the natural tendency for the tissue to slip or creep which ultimately leads to shear and failure. In contrast, the present embodiment takes advantage of this natural action without compromising the integrity of the implant. By looping the tendon a pulley design is created. The cross sectional area of the tendon is doubled, thereby doubling the strength of the single tendon to meet or exceed the 1000N force desired for tendons used is these surgeries. This allows use of a host of other tendons that do not have the strength of a single ACL or PCL. The pulley design overcomes the difficulty of getting two different tendons to bear the same stresses because, through use of a single looped tendon, forces are equalized by natural slippage of the tendon under stress.

Another advantage of the present embodiment is that fixation points are reduced to one, thereby reducing cycling creep by as much as 80% of the gross common when two points of fixation and no stitch augmentation is employed. Double hamstring and double semitendenousus have been used before, but nothing in use today employs cyclic creep to gain a mechanical advantage. In this embodiment, the pulley affect of the mounted bone graft allows the tendon fixed at one point to creep naturally under the sutures, thereby minimizing damage to the fibril structure and the likelihood of shear. Further, using the tendon as a form of rope through a pulley uses the same forces that defeat the attachment problems associated with artificial attachment. In the present embodiment the segmented bone block bears no load along its sides and is in fact aided by the tissue being on both sides of the bone block. Doubling also assures that the upper portion of the tendon receives adequate blood flow from the surrounding tissue.

Using this embodiment two types of fixation are possible based on the length of the tendon; internal interference screw tibial fixation, and exterior fixation. Because the block comprises two segments, bone considered to narrow, too short or too thin for other applications such as an interference screw, may be utilized to create differently sized bone blocks, thereby increasing the yield of this limited resource. Thus, donor specific problems such as finding bone blocks large enough for use is made easier. Further, the use of both long and short tendons of all cross-sectional sizes when paired with different sized segments, allows a physician to attach the block in any fashion of two well accepted methods in use today. Also, because the length may be varied, more tissue would become available for ACL or PCL grafts.

Those skilled in the art will appreciate that the graft may be an autograft, allograft, or xenograft. Xenograft implants may further require treatments to minimize the level of antigenic agents and/or potentially pathogenic agents present in the graft. Techniques now known, or those, which are later developed, for preparing tissue such that it is suitable for and not rejected by the recipient are incorporated herein. In cases where the graft is an allograft or xenograft, a donor is preferably screened for a wide variety of communicable diseases and pathogens, including human immunodeficiency virus, cytomegalovirus hepatitis B, hepatitis C and several other pathogens. These tests may be conducted by any of a number of means conventional in the art, including, but not limited to, ELISA assays, PCR assays, or hemagglutination. Such testing follows the requirements of the following associations: (a) American Association of Tissue Banks. Technical Manual for Tissue Banking, Technical Manual-Musculoskeletal Tissues, pages M19-M20; (b) The Food and Drug Administration, Interim Rule, Federal Register, Vol. 58, No. 238, Tuesday, December 14, Rules and Regulations, 65517, D. Infectious Disease Testing and Donor Screening; (c) MMWR, Vol. 43, No. RR-8, Guidelines for Preventing Transmission of Human Immunodeficiency Virus Through Transplantation of Human Tissue and Organs, pages 4-7; (d) Florida Administrative Weekly, Vol. 10, No. 34, Aug. 21, 1992, 59A-1.001-014, 59A-1.005(12)(c), F.A.C., (12)(a)-(h), 59A-1.005(15, F.A.C., (4) (a)-(8). In addition to a battery of standard biochemical assays, the donor, or their next of kin can be interviewed to ascertain whether the donor engaged in any of a number of high risk behaviors such as having multiple sexual partners, suffering from hemophilia, engaging in intravenous drug use etc. Where allogenic and for xenogenic sources are used, the grafts are preferably treated by techniques described in WO/0009037 and WO/01/08715. Once a donor has been ascertained to be acceptable, the tissue for obtention of the BTBs as described above are recovered and cleaned.

The present invention provides a source for obtaining a quantity of BTBs sufficient to meet the increasing demand for BTBs that heretofore has not been possible through use of human grafts alone. Furthermore, while Applicants have discovered that the anatomical status of non-human knees (e.g., porcine) provide a viable alternative source for procuring BTBs. While the procurement of BTBs from porcine sources is specifically exemplified, it is understood to those skilled in the art, in view of the teachings herein, that other xenograft sources can be used as well including, but not limited to, bovine, equine and other ruminant animals.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 1

Procedure for Harvesting of Crude BTB for Patellar Tendon Tibial Donor

A BTB was harvested according to the following procedure:

1. Using blunt and sharp dissection remove the three layers of connective tissue from the anterior portion of the tendon.
2. Using scalpel or scissors cut along the medial and lateral borders of the tendon. Use the scissors to bluntly dissect under the tendon to separate it from the fat layer.
3. Cut around the Patellar block to separate it form the proximal tibia and distal femur. Leave approximately 4 cm of quadriceps tendon attached to the patellar if required. If no quadriceps tendon attachment is specified then remove quadriceps from patellar completely using sharp dissection.
4. Pull tendon away from capsule and remove all excess adipose tissue to the point of tibial insertion.
5. With a saw make a transverse cut through approximately the tibial tuberosity 10 about 30 mm from the tendon insertion point. Make a similar cut about 5 mm proximal to the insertion point, which will remove the tibial plateau.
6. With a saw, cut and square the sides of the tibia bone block even with the tendon.
7. With a saw cut and square the patella block on three sides (if quadriceps tendon is still attached square off only the medial and lateral sides).
8. Remove all extraneous soft tissue and cartilage from the patella, tibial tuberosity and tendon.
9. To hemisect the patellar tendon use a scalpel to divide the tendon into a medial half and a lateral half. Each half should be 14 mm or greater unless otherwise specified.
10. Using a saw, split the patella block and the tibia block in half following the same medial/lateral line used to split the tendon.
11. Thoroughly lavage the bone blocks with sterile water or saline.

EXAMPLE 2

Procedure for Forming Patellar Tendons with Reshaped Dowels for Patellar Tendon Tibial Donor A BTB was harvested according to the following procedure:

1. Using blunt and sharp dissection remove the three layers of connective tissue from the anterior portion of the tendon.
2. Using a scalpel or scissors cut along the medial and lateral borders of the tendon to separate it from the fat layer.
3. Cut around the Patellar block to separate it from the proximal tibia and distal femur.
4. Pull tendon away from capsule and remove all excess adipose tissue to the point of tibial insertion.
5. With a saw make a transverse cut through the tibial tuberosity about 30 mm from the tendon insertion point. Make a similar cut just proximal to the insertion point removing the tibial plateau. Make another cut across the coronal plane 20-30 mm posterior from the insertion point.
6. With a saw square the sides of the tibia bone block.
7. With a saw cut and square the patella block on the three sides.
8. Attach a vice to the tabletop. Place the tibia bone block in the vice so that it holds it along the proximal and distal sides. The distal side of the bone block should be facing the processor with the tendon going away from them. Tighten the vice so that it holds the bone securely but does not crush it.
9. Attach a Jacob's chuck to a drill and insert the appropriate size cutter. Tighten the chuck with the chuck key. Note: At least two plugs should be cut from each bone block.
10. Position the cutter against the bone block so the teeth of the cutter will skim just over the top of the tendon without catching the tendon. Position the cutter so that the maximum attachment is obtained throughout the length of the bone plug.
11. Turn drill on and begin drilling the plug. When the cutter nears the end of the plug, slow the drill until the cutter just breaks through the proximal end of the bone block. Remove the plug from the cutter and drill without damaging the tendon.
12. Repeat steps 10 and 11 for the second plug.
13. Using scissors or a scalpel hemisect the tendon into medial and lateral halves.
14. Remove the excess bone from the table vice and place the patella bone block into the vice so that it holds it along the medial and lateral sides of the block. The proximal side of the patella should be facing the processor with the tendon going away from them. Tighten the vice so that it holds the bone block securely but does not crush it.
15. Repeat steps 10 and 11 for both plugs.
16. When the plugs are completed, remove the excess patella bone from the vice and detach the vice from the table.
17. Remove the cutter from the Jacob's chuck and place a 1.5 mm drill bit into the chuck. Tighten with the chuck key.
18. Using a saw, cut each plug to approximately 30 mm in length (no less than 45 25 mm)
19. Using the Arthrex clamp, place the plug into it with the end of the plug flush with the end of the clamp. Position the plug in the anterior/posterior position. Using the first guide hole nearest the flush end of the plug, drill a hole through the plug with the 1.5 mm drill bit. Turn the plug 180 degrees so that it is positioned in the medial/lateral position. Use the second guide hole from the flush end of the plug to drill a second hole through the plug.

20. Repeat step 19 for all bone plugs.

21. Using a sizing apparatus insert each bone plug into the appropriate size gauge. The entire BTB should slide completely through easily. Trim if necessary.

22. Thoroughly lavage bone plugs with sterile water or saline.

EXAMPLE 3

Production of Porcine BTB

A tissue sample was harvested from a pig knee to form a traditionally shaped BTB shown in FIGS. 9A, 9B and 9C according to the above disclosed method. The graft measured 65 mm (1)×14 mm (w), with a total length of 131 mm and thickness of 6 mm. The tibia block measured 35 mm (1)×16 mm (w)×12 mm (h) and the patellar block measured 32 mm (1)×16 mm (w)×17 mm (h). The graft looked similar to a human BTB graft, and had a very dense, cancellous bone on the patella and tibia.

EXAMPLE 4

Load to Failure Data for two Porcine Grafts

Two porcine BTBs were harvested and pre-shaped according to the disclosed method from pig knees for testing of maximum strength. Specimen 1 measured 79 mm (1)×11 mm (w), and was 4.5 mm thick. The tibia bone block measured 21 mm (1)×9.5 mm (w)×9.5 mm (h) and the patella bone block measured 3.6 mm (1)×9.6 (w)×9.5 mm (h). The graft failed at the tendon at maximum load of 1055N. Specimen 2 measured 63 mm (1)×13 mm (w), and was 6.0 mm thick. The tibial bone block measured 26 mm (1)×9.6 mm (w)×9.5 mm (h), while the patellar bone block measured 29 mm (1)×9.7 mm (w)×9.5 mm (h). The graft failed at a maximum load of 1187 N.

What is claimed:

1. An assembled graft useful in orthopedic surgery comprising a tendon and a first bone block comprising bone having a first machined shape, wherein said first bone block is segmented into upper and lower halves; said tendon having a first end and a second end, said first end affixed to said first bone block, said tendon connecting to said first bone block and forming said assembled graft, and wherein said bone block comprises a solid exterior surface and said bone block further comprises an interior having multiple compartments to accommodate and hold in place said tendon; wherein said multiple compartments comprise at least one interior receiving chamber and at least one interior fixation chamber.

2. The assembled graft of claim 1, wherein a portion of said first bone block is demineralized cortical bone.

3. The assembled graft of claim 1, wherein said first bone block is allograft bone.

4. The assembled graft of claim 1, wherein said first bone block is xenograft bone.

5. The assembled graft of claim 1, wherein said compartments further comprise an interior receiving chamber which funnels down to an interior fixation chamber opening, leading to an interior fixation chamber.

6. The assembled graft of claim 1, wherein said tendon creates a pulley design which employs cyclic creep to gain a mechanical advantage.

7. The assembled graft of claim 1, wherein said graft further comprises at least a first fastener device and a second fastener device.

8. The assembled graft of claim 7, wherein said first fastener device is fixed longitudinally or laterally while said second fastener device is allowed to rock over said first fastener device.

9. The assembled graft of claim 1, wherein said tendon is impregnated or coated with bone particles or chips.

10. The assembled graft of claim 1, wherein said tendon comprises an Achilles tendon, and said first bone block comprises calcaneal bone.

* * * * *